United States Patent
Leighton

(10) Patent No.: US 8,592,381 B2
(45) Date of Patent: Nov. 26, 2013

(54) METHOD FOR TREATING RHINITIS AND SINUSITIS BY RHAMNOLIPIDS

(75) Inventor: Anton Leighton, Oakland, CA (US)

(73) Assignee: Rhamnopharma Inc., Oakland, CA (US)

( * ) Notice: Subject to any disclaimer, the term of this patent is extended or adjusted under 35 U.S.C. 154(b) by 29 days.

(21) Appl. No.: 13/160,322

(22) Filed: Jun. 14, 2011

(65) Prior Publication Data

US 2011/0257115 A1 Oct. 20, 2011

Related U.S. Application Data

(63) Continuation-in-part of application No. PCT/US2009/068111, filed on Dec. 15, 2009.

(60) Provisional application No. 61/138,917, filed on Dec. 18, 2008, provisional application No. 61/145,493, filed on Jan. 16, 2009, provisional application No. 61/355,293, filed on Jun. 16, 2010.

(51) Int. Cl.
*A61K 31/70* (2006.01)

(52) U.S. Cl.
USPC ............................................................ 514/25

(58) Field of Classification Search
USPC ............................................................ 514/25
See application file for complete search history.

(56) References Cited

U.S. PATENT DOCUMENTS

| 5,514,661 | A | 5/1996 | Piljac et al. |
| 7,129,218 | B2 * | 10/2006 | Stipcevic et al. ............... 514/25 |
| 7,261,171 | B2 | 8/2007 | de la Torre et al. |
| 7,378,082 | B1 | 5/2008 | Krishnamoorthy |
| 2005/0031549 | A1 | 2/2005 | Quay et al. |
| 2007/0077283 | A1 * | 4/2007 | Quay et al. .................... 424/448 |

OTHER PUBLICATIONS de Benedictis et al. Rhinitis, sinusitis, and asthma: one linked airway disease. Paediatr Respir Rev 2:358-364, Dec. 2001.*
International Search Report mailed Feb. 19, 2010 fpr PCT/US09/68111.
Rhamnolipid, Inc. Rhamnolipid Basics. Published Apr. 19, 2008, p. 1 [online], document retrieved on Jan. 25, 2010, [retrieved from http://web.archive.orglweb/20080419011148/www.rhamnolipid.com/rhamnolipidbasics.html], especially, p. 1, para 3.

* cited by examiner

*Primary Examiner* — Wu-Cheng Winston Shen
*Assistant Examiner* — Yih-Horng Shiao
(74) *Attorney, Agent, or Firm* — Perkins Coie LLP.; Viola T. Kung

(57) ABSTRACT

The present invention is directed to methods for treating rhinitis or sinusitis in a subject. In one embodiment, the method comprises the steps of: identifying a subject in need thereof, and administering intranasally to the subject a formulation comprising an only active ingredient of an effective amount of rhamnolipid. In another embodiment, the method comprises the steps of: identifying a subject in need thereof, and administering intranasally to the subject a first active ingredient of an effective amount of a rhamnolipid and a second active ingredient of an effective amount of a corticosteroid, an antihistamine, a leukotriene antagonist, cromylin, an antibiotic, a sphingolipid, or a decongestant.

10 Claims, No Drawings

METHOD FOR TREATING RHINITIS AND SINUSITIS BY RHAMNOLIPIDS

This application is a continuation-in-part of PCT/US2009/068111, filed Dec. 15, 2009; which claims the priority of U.S. Provisional Application Nos. 61/138,917, filed Dec. 18, 2008 and 61/145,493, filed Jan. 16, 2009. This application also claims the benefit of U.S. Provisional Application No. 61/355,293, filed Jun. 16, 2010. The contents of the above-identified applications are incorporated herein by reference in their entirety.

FIELD OF THE INVENTION

This invention relates to methods of treating rhinitis and sinusitis by intranasal delivery of active ingredient of a rhamnolipid alone or in combination with a corticosteroid, an antihistamine, an anticholinergic agent, a leukotriene antagonist, cromolyn, an antibiotic, a decongestant, or a surfactant.

BACKGROUND OF THE INVENTION

Rhinitis is a term describing the symptoms produced by nasal irritation or inflammation. Symptoms of rhinitis include runny nose, itching, sneezing and stuffy nose due to blockage or congestion. These symptoms are the nose's natural response to inflammation and irritation, and they are often associated with itching of the eyes.

The nose normally produces mucus, which traps substances like dust, pollen, pollution, and germs such as bacteria and viruses. Mucus flows from the front of the nose and drains down the back of the throat. When mucus production is excessive, it can flow from the front, as a runny nose, or become noticeable from the back, as post-nasal drip. Nasal mucus, normally a thin, clear liquid, can become thick or colored, perhaps due to dryness, infection or pollution. When post-nasal drip is excessive, thick, or contains irritating substances, cough is the natural response for clearing the throat.

Itching and sneezing are also natural responses to irritation caused by allergic reactions, chemical exposures including cigarette smoke, or temperature changes, infections and other factors.

The nasal tissues congest and decongest periodically. In most people, nasal congestion switches back and forth from side to side of the nose in a cycle several hours long. Some people, especially those with narrow nasal passages, notice this nasal cycle more than others. Severe congestion can result in facial pressure and pain, as well as dark circles under the eyes.

The three most common types of rhinitis are allergic, infectious, and non-allergic. Infectious rhinitis (colds or flu) are typically caused by viruses; its duration is often 3 to 7 days, and sometimes longer. Colds usually begin with a sensation of congestion, rapidly followed by runny nose and sneezing. Over the next few days, congestion becomes more prominent, the nasal mucus may become colored, and there may be a slight fever and cough. Cold symptoms resolve within a couple of weeks, although a cough may sometimes persist. Cold symptoms that last longer may be due to other causes, such as chronic rhinitis or sinusitis.

Non-allergic rhinitis refers to rhinitis having symptoms not caused by infection or allergy. Non-allergic rhinitis includes vasomotor rhinitis and irritant rhinitis. Many people have recurrent or chronic nasal congestion, excess mucus production, itching, and other nasal symptoms similar to those of allergic rhinitis, but the disorder is not caused by allergy. Irritants that can trigger vasomotor rhinitis include cigarette smoke, strong odors and fumes including perfume, hair spray, cosmetics, laundry detergents, cleaning solutions, pool chlorine, car exhaust and other air pollution. Other irritants are spices used in cooking, alcoholic beverages (particularly beer and wine), aspirin, and certain blood pressure medications. Some people are very sensitive to abrupt changes in weather or temperature. Skiers often develop a runny nose, but in some people any cold exposure may cause a runny nose. Others start sneezing when leaving a cold, air conditioned room. The duration of symptoms of non-allergic rhinitis can be perennial and/or following exposure.

Allergic rhinitis, also known as hay fever, is often caused by dust mites, animals, pollens, molds, and food. Allergic rhinitis is an inflammatory state characterized by numerous symptoms such as nasal congestion, nasal discharge, post-nasal drip, sore throat, sneezing, headache, itching of the nose and throat, facial pressure and pain, and general malaise. Settipane et al (Ann. Allergy Asthma Immunol. 86:494-508 (2001)) report that allergic rhinitis is about 3 times more prevalent than pure nonallergic rhinitis; however, a mixed picture of the two is quite common: it is estimated that 44% to 87% of patients with rhinitis have some component of mixed rhinitis.

Perennial allergic rhinitis (PAR) is the most common type of allergic rhinitis, and is typically caused by exposure to allergens such as mold spores, dust mites, animal dander and others, and can occur at any time of year. This is generally viewed as a chronic disease. Seasonal allergic rhinitis, also known as hay fever, is a reaction to pollen or mold and typically occurs during certain seasons, for example during "rag weed season" in certain locals. The duration of the allergic reactions can be several days to a few months. Occupational allergic rhinitis is similar to PAR, but it is triggered by a response to airborne allergens at work. Infectious allergic rhinitis occurs during an upper respiratory infection, such as during the common cold, in which the infecting organism releases inflammatory mediators that trigger an allergic response. Symptoms last throughout the time of infection and are often associated with an increase in sinus and bronchial infections. Hormonal allergic rhinitis occurs typically during pregnancy or in patients with other hormonal imbalances such as hypothyroidism. Idiopathic allergic rhinitis is a term used to describe allergic rhinitis in which either the allergen is not known or the cause of the inflammatory rhinitis symptoms is best defined as perennial non-allergic.

Allergic rhinitis clinically presents as some or all of the following symptoms: rhinorrhea, sneezing, nasal congestion, itching of the nose and palate, and ocular symptoms (itchy, watery eyes). (Skoner D P. Allergic rhinitis: definition, epidemiology, pathophysiology, detection, and diagnosis. *J Allergy Clin Immunol* 2001; 108 (1 Suppl): S2-S8)

There is a close correlation between inflammatory mediators in nasal secretions and symptoms of Allergic Rhinitis. (Lebel B, Bousquet J, Morel A, et al. Correlation between symptoms and the threshold for release of mediators in nasal secretions during nasal challenge with grass-pollen grains. *J Allergy Clin Immunol* 1988; 82(5 Pt 1):869-877)

Cytokines and chemokines, such as interleukin (IL)-8, as well as the mediators released by the early-phase reaction, help recruit and activate inflammatory cells, such as eosinophils, which themselves release mediators. (White M. Mediators of inflammation and the inflammatory process. *J Allergy Clin Immunol* 1999; 103(3 Pt 2):S378-S381)

Symptoms are therefore perpetuated, with persistent allergic rhinitis sufferers existing in a continual state of eosinophilia and increased mediator release. (Wang D Y, Clement P.

Pathogenic mechanisms underlying the clinical symptoms of allergic rhinitis. *Am J Rhinol* 2000; 14:325-333)

Eosinophils express various membrane molecules, including FcεRI. (Capron, M., Soussi Gounni, A., Morita, M., Truong, M. J., Prin, L., Kinet, J. P. Capron, A. Eosinophils: from low- to high-affinity immunoglobulin E receptors. *Allergy* 1995, 50 (25 Suppl):20-23.)

Binding of the allergen-IgE complex with FcεRI on the eosinophil surface results in signal transduction, which activates the cell to release preformed, granule-associated proteins, arachidonic acid-derived products, cytokines and oxygen free radicals. (Capron, M., Desreumaux, P. Immunobiology of eosinophils in allergy and inflammation. *Res Immunol* 1997, 148:29-33)

A significant eosinophil activation may occur also in the very early events characterizing the reaction to allergen exposure. (Sihra, B. S., Kon, O. M., Grant, J. A., Kay, A. B. Expression of high-affinity IgE receptors (Fc epsilon RI) on peripheral blood basophils, monocytes and eosinophils in atopic and nonatopic subjects: relationship to total serum IgE concentrations. *J Allergy Clin Immunol* 1997, 99:699-706.)

In addition to mast cells and eosinophils, epithelial cells are also activated after allergen challenge. [Ciprandi, G., Pronzato, C., Ricca, V., Passalacqua, G., Bagnasco, M., Canonica, G. W. Allergen-specific challenge induces intercellular adhesion molecule 1 (ICAM-1 or CD54) on nasal epithelial cells in allergic subjects. Relationships with early and late inflammatory phenomena. *Am J Respir Crit Care Med* 1994, 150:1653-1659. Vignola, A. M., Campbell, A. M., Lacoste, P., Michel, F. B., Godard, P., Bousquet, J. Activation by histamine of bronchial epithelial cells from non asthmatic subjects. *Am J Respir Cell Mol Biol* 1993, 9:411-417.

Allergic rhinitis and asthma are closely-related entities influenced by common pathogenetic processes, linked by similar physiologic characteristics, sustained and amplified by interconnected mechanisms in atopic individuals. A recent clinical study has shown close correlations between bronchial reactivity and eosinophil percentages in nasal brushing, 'at baseline' and after nasal allergen challenge. (Silvestri M, Battistini E, Defilippi A-C, Sabatini F., Sale R, Pecora S, and Rossi G A. *J Invest Allergol Clin Immunol* 2005; Vol. 15(4): 266-276)

Allergic rhinitis is an inflammatory reaction, where a high degree of cell-to-cell communication is needed to orchestrate this inflammatory immune response. A variety of cytokines and adhesion receptors play an important role in the allergic late phase reaction. (C. Bachert, U. Hauser, B. Prem, C. Rudack and U. Ganzer. Proinflammatory cytokines in allergic rhinitis. European Archives of Oto-Rhino-Laryngology Volume 252, Supplement 1/January, 1995)

Sinusitis (rhinosinusitis) is inflammation or infection of any of the four groups of sinus cavities in the skull, which open into the nasal passages. Sinusitis is not the same as rhinitis, although the two may be associated and some of their symptoms may be similar. Sinusitis affects approximately 16% of U.S. adults. Viral upper respiratory tract infections and allergic rhinitis, which affects up to 35.9 million Americans each year, are the two most common predisposing conditions for sinusitis. Medical treatments that are useful in treating recurrent acute and chronic sinusitis include the same range of medications as used for rhinitis, such as intranasal corticosteroids and decongestants. A course of oral antibiotics may be indicated for sinusitis.

Coexisting sources of nasal inflammation can manifest themselves with similar symptoms and can participate in the diffuse problem of sinusitis. There is histopathologic evidence that rhinitis was associated with chronic sinusitis. Several of the consensus documents mentioned above, most recently that published simultaneously in the Journal of Allergy and Clinical Immunology and Otolaryngology—Head and Neck Surgery in December 2004, officially adopted the term rhinosinusitis in preference to sinusitis. (Rhinosinitis and the revised "Sinusitis practice parameters". Hamilos D L et al. J Allergy and Clin Immunol. December 2005)

Rhamnolipids are naturally occurring biosurfactants constructed of rhamnose sugar molecules and β-hydroxyalkanoic acids. Production of rhamnose containing glycolipids was first described in *Pseudomonas aeruginosa* by Jarvis and Johnson. (Jarvis, F. G. and Johnson, M. J., A glycolipid produced by *Pseudomonas aeruginosa*. J. Am. Oil Chem. Soc., 1949, 71, 4124-4126.)

L-Rhamnosyl-L-rhamnosyl-β-hydroxydecanoyl-β-hydroxydecanoate and L-rhamnosyl-β-hydroxydecanoyl-β-hydrocydecanoate, are the principal glycolipids produced by *P. aeruginosa*. (Edward, J. R. and Hayashi, J. A., Structure of rhamnolipid from *Pseudomonas aeruginosa*. Arch. Biochem. Biophys., 1965, 111, 415-421.)

Rhamnolipids have demonstrated low irritancy and even anti-irritating effects when used topically on the skin. (Stipcevic T, et al. J Dermatol Sci. 2005 November; 40(2): 141-143.)

U.S. Pat. No. 7,261,171 discloses the use of rhamnolipids in re-epithelization of skin, particularly in wound healing with the diminution of fibrosis.

U.S. Pat. No. 5,514,661 discloses the use of rhamnolipids for treating autoimmune diseases of organ specific and organ non-specific autoimmune diseases, AIDS, Parkinson's disease, Alzheimer's disease and amyotrophic lateral sclerosis.

There is a need for improved methods for treating rhinitis and sinusitis. The method should be safe, effective and have no significant side effects.

SUMMARY OF THE INVENTION

The present invention is directed to methods for treating rhinitis or sinusitis, in a subject. In one embodiment, the method comprises the steps of: identifying a subject in need thereof, and administering intranasally to the subject a formulation comprising an active ingredient of an effective amount of rhamnolipid only. In another embodiment, the method comprises the steps of: identifying a subject in need thereof, and administering intranasally to the subject a first active ingredient of an effective amount of a rhamnolipid and a second active ingredient of an effective amount of a corticosteroid, an antihistamine, a leukotriene antagonist, cromylin, an antibiotic, a decongestant, a biosurfactant, or any combinations of the aforementioned ingredients.

Corticosteroids useful in combination with rhamnolipids in the present invention include budesonide, ciclesonide, flunisolide, fluticasone, mometasone, triamcinolone or dexamethasone. Antihistamines useful in combination with rhamnolipids in the present invention include azelastine, olopatadine, or loratadine. Anticholinergic agents useful in combination with rhamnolipids in the present invention include ipratropium bromide. Decongestants useful in combination with rhamnolipids in the present invention include oxymetazoline.

Leukotriene antagonists useful in combination with rhamnolipids in the present invention include montelukast (Singulair) and zafirlukast (Accolate).

Antibiotics useful in combination with rhamnolipids in the present invention include penicillin, amoxicillin, augmentin, a cephalosporin, a macrolide such as erythromycin, an aminoglycoside such as gentamicin, a fluoroquinolone such as ciprofloxacin, a tetracycline or tetracycline derivate.

DETAILED DESCRIPTION OF THE INVENTION

The inventor has discovered that rhamnolipids, when used as a topical agent and intranasally administered to a person with allergic rhinitis, provide rapid and protracted alleviation of symptoms of allergic rhinitis, for up to 12 hours. The inventor also discovered that rhamnolipids, when used as a topical agent and intranasally administered to a patient, improved rhinorrhea, nasal congestion, nasal itching, or sneezing.

The present invention is directed to a method for treating rhinitis. The method comprises the steps of: identifying a subject suffering from rhinitis, and administering intranasally to the subject a pharmaceutical formulation in which the active ingredient comprises an effective amount of rhamnolipid, whereby the symptoms of rhinitis in the subject are reduced. "The effective amount," as used herein, refers to an amount that alleviates or reduces one or more symptoms of rhinitis such as nasal congestion, nasal discharge, post-nasal drip, sore throat, sneezing, headache, itching of the nose and throat, facial pressure and pain, and general malaise.

The present invention is suitable to treat rhinitis including allergic rhinitis, infectious rhinitis, and non-allergic rhinitis. Allergic rhinitis is caused by allergens and affects more than 15 percent of adults and children. Allergic rhinitis includes seasonal allergic rhinitis (also called hay fever) and perennial allergic rhinitis. Seasonal allergic rhinitis is caused by outdoor allergens like pollen and mold. Perennial allergic rhinitis is caused by indoor allergens like animal dander and dust mites. Symptoms of allergic rhinitis include sneezing, runny nose, and nasal congestion. There may also be itching in the eyes, ears, nose and roof of the mouth.

Infectious rhinitis is caused by a common cold. Infections usually are self-limiting and subside after about a week. Infectious rhinitis symptoms that last longer may be due to a noninfectious rhinitis. Symptoms of infectious rhinitis include nasal congestion, runny nose, sneezing, fever and coughing.

Many people who suffer from rhinitis do not have an allergy or an infection. Non-allergic rhinitis has many triggers including smoke, cooking odors, spicy foods and certain medications. The cause of non-allergic rhinitis is still not fully understood, but the symptoms are similar to those of allergic rhinitis and sometimes include excess mucus production, congestion and itching.

The present invention is suitable to treat allergic rhinitis such as perennial, seasonal, and idiopathic allergic rhinitis. The present invention is also suitable to treat non-allergic rhinitis such as vasomotor, occupational, and hormonal rhinitis. The present invention is also suitable to treat mixed allergic rhinitis and non-allergic rhinitis.

The present invention is also directed to a method for treating sinusitis. The method comprises the steps of: identifying a subject suffering from sinusitis, and administering intranasally to the subject a pharmaceutical formulation in which the active ingredient is rhamnolipid only in an effective amount, whereby the symptoms of sinusitis in the subject are reduced. "The effective amount," as used herein, refers to an amount that alleviates or reduces one or more symptoms of sinusitis such as nasal congestion, increased nasal secretions (rhinorrhea), nasal itching, sneezing.

Rhamnolipids are biosurfactants containing rhamnose sugar molecules and β-hydroxyalkanoic acids. Rhamnolipids suitable to be used in the present invention include natural rhamnolipids, for example, obtained from *Pseudomonas aeruginosa*; rhamnolipids produced by any Pseudomonad, including *P. chlororaphis, Burkholdera pseudomallei, Burkholdera* (*Pseudomonas*) *plantarii*, and any recombinant Pseudomonad. Suitable rhamnolipids also includes those produced by other bacteria or by plants either naturally or through (genetic) manipulation. Suitable rhamnolipids further include rhamnolipids and their analogs prepared by chemical synthesis. Suitable rhamnolipids include those disclosed in U.S. Pat. Nos. 7,262,171 and 5,514,661, in which the structures of rhamnolipids are incorporated herein by reference.

Preferred rhamnolipids are L-rhamnosyl-β-hydroxydecanoyl-β-hydrocydecanoate (rhamnolipids 1) and L-rhamnosyl-L-rhamnosyl-β-hydroxydecanoyl-β-hydroxydecanoate (rhamnolipids 2), and the mixture thereof.

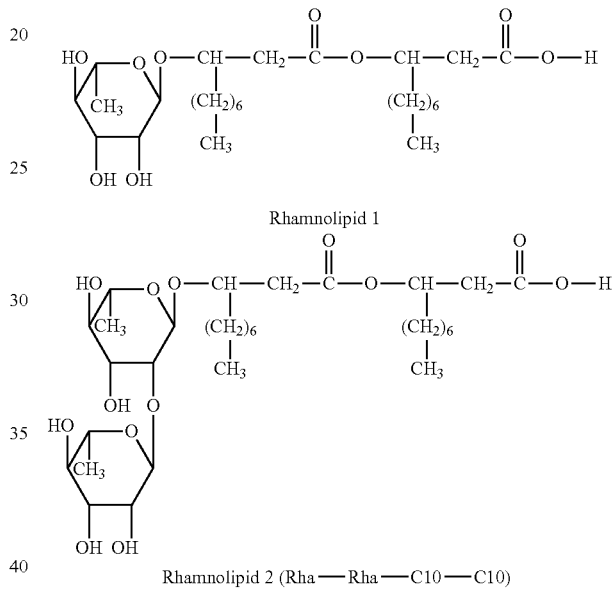

Rhamnolipid 1

Rhamnolipid 2 (Rha—Rha—C10—C10)

Some other common di-rhamnolipids useful for this invention include: L-rhamnopyranosyl-L-rhamnopyranosyl-beta-hydroxydecanoyl-beta-hydroxydodecanoate (often referred to as Rha-Rha-C10-C12); L-rhamnopyranosyl-L-rhamnopyranosyl-beta-hydroxytetradecanoyl-beta-hydroxytetradecanoate (often referred to as Rha-Rha-C14-C14).

In one embodiment, the method of the present invention comprises co-administering one or more second active ingredients such as corticosteroids, antihistamines, anticholinergic agents, leukotriene antagonists, cromolyn, decongestants, a sphingolipid, and/or antibiotics. In the present invention, the active ingredients do not include growth hormone.

An anticholinergic agent is a substance that blocks the neurotransmitter acetylcholine in the central and the peripheral nervous system. An example of an anticholinergic is dicyclomine, and the classic example is atropine. Anticholinergics are administered to reduce the effects mediated by acetylcholine on acetylcholine receptors in neurons through competitive inhibition.

A leukotriene antagonist (montelukast, zafirlukast and zileuton) is a drug that inhibits leukotrienes, which are compounds produced by the immune system that cause inflammation in the respiratory tract. Leukotriene antagonists are less effective than corticosteroids, but have virtually no side effects, so they are often used to treat children.

Cromolyn (also referred to as cromoglicic acid, cromoglycate, or cromoglicate) is traditionally described as a mast cell stabilizer, and is commonly marketed as the sodium salt sodium cromoglicate or cromolyn sodium. This drug prevents the release of inflammatory chemicals such as histamine from mast cells.

A decongestant or nasal decongestant is a type of drug which is used to relieve nasal congestion. Decongestant nasal sprays and often contain oxymetazoline and are used for topical decongestion.

Sphingolipids are a class of lipids derived from the aliphatic amino alcohol sphingosine.

Intranasal corticosteroids such as budesonide, ciclesonide, flunisolide, fluticasone, mometasone or triamcinolone, when used in combination with rhamnolipids, increase and prolong the overall treatment effect of rhamnolipid.

Antihistamines such as azelastine, olopatadine, or loratadine, and decongestants such as oxymetazoline, when used in combination with rhamnolipids, provide synergistic treatment effect by adding a more rapidly acting and longer decongestant effect in comparison with a single drug treatment.

A combination of rhamnolipid with cromolyn is expected to be synergistic in their antihistamine effect and thus offer increased reduction in rhinitis symptoms when compared to cromolyn alone. A combination of rhamnolipid and cromolyn reduces symptoms faster and reduces the required frequency of application of cromolyn.

A combination of rhamnolipid with anticholinergic agents (such as ipratropium) decreases nasal drainage mediated by neural pathways in some cases of rhinitis, and thus increases and expands the effect of rhamnolipids.

A combination of a rhamnolipid and a leukotriene antagonist is expected to provide synergistic effects due to a broader range of inhibition of inflammatory pathways.

A combination of a rhamnolipid and a surfactant or biosurfactant such as sphingolipid is expected to provide synergistic effects due to a broader range of inhibition of inflammatory pathways.

A combination of a rhamnolipid and an antiviral agent is expected to provide synergistic effects in cases of viral rhinitis.

Short term (up to 3-4 days) treatment of oxymetazoline and related decongestants (such as ephedrine, levomethamphetamine, naphazoline, oxymetazoline, phenylephrine, pseudoephedrine, tramazoline, xylometazoline) in combination with rhamnolipids leads to a rapid onset and therefore early benefit of treatment effects in comparison with a single drug treatment.

A combination of rhamnolipid and one or more antibiotics is useful to treat the concurrent bacterial infection in sinusitis or rhinitis.

Rhamnolipids, and the second active ingredient such as corticosteroids, antihistamines, cromolyn, leukotriene antagonists, decongestants and antibiotics, can either be separately administered to a patient, or they can be combined in one formulation and then administered to a patient.

The pharmaceutical formulation used for this invention typically contains pure rhamnolipid(s) and a pharmaceutically acceptable carrier in an aqueous solution. The concentration of rhamnolipid(s) is in a topical formulation is in general 0.005-10% (w/w), or 0.02-5%, or 0.1-5%, or 0.2 to 5%, or 0.2-2%, or 0.05-0.5% (w/w). In one embodiment, the concentration of rhamnolipid(s) is about 0.5% (w/w). "About" as used herein, refers to ±10% of the recited value. The concentration can be higher or lower as long as it delivers an effective and tolerable dose per surface of nasal mucosa per dosing interval. For example, a lower concentration can be used for irrigation, and a higher concentration can be used for inhalation.

In addition to rhamnolipids at the above-described concentration, the pharmaceutical formulation can further contain one or more corticosteroids, antihistamines, anticholinergic agent, a leukotriene antagonist, cromolyn, a decongestant, a biosurfactant, and/or antiviral drug. For example, the pharmaceutical formulation may further contain 0.01-0.06% w/v of a corticosteroid (budesonide, ciclesonide, flunisolide, fluticasone, mometasone, triamcinolone or dexamethasone), in addition to rhamnolipids. The pharmaceutical formulation may further contain 0.05-0.2% w/v, preferably 0.1-0.15% w/v of azelastine, in addition to rhamnolipids. The pharmaceutical formulation may further contain 0.2-0.665% w/v of olopatadine, in addition to rhamnolipids. The pharmaceutical formulation may further contain 0.01-0.06% w/v, preferably 0.02-0.06% w/v of ipratropium bromide, in addition to rhamnolipids. The pharmaceutical formulation may further contain 0.01-0.05% w/v of oxymetazoline, in addition to rhamnolipids. The pharmaceutical formulation may further contain 0.5-2.5% w/v, preferably 1-2% w/v of cromolyn, in addition to the rhamnolipids. The pharmaceutical formulation may further contain 0.005-1% w/w, preferably 0.05-0.5% w/w of sphingolipid, in addition to rhamnolipids.

Pharmaceutically acceptable carriers can be selected by those skilled in the art using conventional criteria. Pharmaceutically acceptable carriers include, but are not limited to, sterile water or saline solution, aqueous electrolyte solutions, isotonicity modifiers, water polyethers such as polyethylene glycol, polyvinyls such as polyvinyl alcohol and povidone, cellulose derivatives such as methylcellulose and hydroxypropyl methylcellulose, polymers of acrylic acid such as carboxypolymethylene gel, nanoparticles, polysaccharides such as dextrans, and glycosaminoglycans such as sodium hyaluronate and salts such as sodium chloride and potassium chloride.

In one embodiment, the pharmaceutical formulation of the present invention provides an aqueous solution comprising water, suitable ionic or non-ionic tonicity modifiers, suitable buffering agents, and rhamnolipids. In one embodiment, the rhamnolipid is at 0.005-10% (w/w), and the aqueous solution has a tonicity of 200-400 mOsm/kG and a pH of 4-9.

The pharmaceutical formulation is preferably formulated to have pH between 4.5-8, more preferably 5-7.4. The topical formulation may contain a buffer to facilitate a stable pH of 5-7.4.

The pharmaceutical formulation optionally contains non-ionic tonicity agents such as mannitol, sucrose, dextrose, glycerol, polyethylene glycol, propylene glycol, or ionic tonicity agent such as sodium chloride. The pharmaceutical formulation can further contains ionic or non-ionic surfactants, bile salts, phospholipids, cyclodextrins, micelles, liposomes, emulsions, polymeric microspheres, nanoparticles, or their combination.

The pharmaceutical formulation is applied directly intranasally 1-3 times daily, preferably 1-2 times daily, until major symptoms of allergic rhinitis are eliminated. Then the frequency of applying the topical formulation is slowly reduced and is applied as required to alleviate symptoms of allergic rhinitis.

The topical formulation may contain preservation agents.

The pharmaceutical formulation is preferred to be stable at room temperature for at least 6 months, 12 months, preferably 24 months, and more preferably 36 months. Stability, as used herein, means that rhamnolipid maintains at least 80%, preferably 85%, 90%, or 95% of its initial activity value.

The pharmaceutical formulations of the present invention can be prepared by aseptic technique. The purity levels of all materials used in the preparation preferably exceed 90%.

The pharmaceutical formulation of the present invention is administered locally to the nose in the form of nasal preparations. The pharmaceutical formulation can be administered to the nasal cavity of a patient topically by any suitable means, but is preferably administered in the form of drops or spray; with spray being more preferred. For topical nasal administration, one or two sprays per nostril of the formulation are delivered to the surface of the nose one to three times, preferably two times per day, according to the routine discretion of a skilled clinician. The pharmaceutical formulation can also be inhaled by the subject using a nebulizer The pharmaceutical formulation can also be applied to the intranasal areas of a subject by Q-tip or other similar means.

The pharmaceutical formulation is preferably packaged in opaque plastic containers equipped with a nasal spray pump for topical nasal delivery.

The pharmaceutical formulation of the present invention can be used to prevent or treat diseases or disorders related to allergic and inflammatory diseases of the nose. For example, the pharmaceutical formulation is useful for treating seasonal and perennial allergic rhinitis, infectious rhinitis, vasomotor rhinitis, and sinusitis.

In one embodiment, the present method for treating rhinitis and sinusitis comprises the steps of separately administering a rhamnolipid and a second active ingredient such as corticosteroids, antihistamines, anticholinergic agents, leukotriene antagonists, cromolyn, biosurfactants such as sphingolipids, and/or decongestants.

The present invention provides a method for treating rhinitis. The method comprises identifying a subject suffering from rhinitis, administering intranasally to the subject a first formulation comprising a first active ingredient of a rhamnolipid, and administering to the subject a second formulation comprising a second active ingredient of a corticosteroid, an antihistamine, an anticholinergic agent, a leukotriene antagonist, cromolyn, or a decongestant. The rhamnolipid and the second active ingredient are administered separately often in their usual dosage.

The present invention provides a method for treating sinusitis. The method comprises identifying a subject suffering from sinusitis, administering intranasally to the subject a first formulation comprising a first active ingredient of a rhamnolipid, and administering to the subject a second formulation comprising a second active ingredient of a corticosteroid, an antihistamine, a leukotriene antagonist, cromolyn, an anticholinergic agent, or a decongestant.

When the rhamnolipid and the second active ingredient are administered separately, they are often administered in their usual dosage. The usual dosages of the second active ingredients are listed below. The second active ingredient can be administered topically (spray, solution, etc) to the nasal membrane, or administered orally.

For topical administration of corticosteroids, budesonide (brand name Rhinocort Aqua) is usually used 1-4 sprays per nostril per day at 32 µg/spray. Ciclesonide (brand name Omnaris Nasal Spray) is usually used 2 sprays per nostril per day at 50 µg/spray. Flunisolide is usually used 1-2 sprays per nostril, 2-4 times per day, at 29 µg/spray. Fluticasone propionate (brand name Flonase Nasal Spray) is usually used 1-2 sprays per nostril per day at 50 µg/spray. Fluticasone furoate (brand name Veramyst Nasal Spray) is usually used 1-2 sprays per nostril per day at 27.5 µg/spray. Mometasone furoate monohydrate (brand name Nasonex Nasal Spray) is usually used 1-2 sprays per nostril per day at 50 µg/spray. Triamcinolone acetonide (brand name Nasacort AQ) is usually used 1-2 sprays per nostril per day at 55 µg/spray.

For oral administration of corticosteroid, 1-2 mg of betamethasone is usually given once per day, 50-75 mg of predenisolone is usually given once per day, 4-8 mg of dexamethasone is usually given once per day.

For antihistamines, azelastine, brand names Astelin Nasal Spray, is usually used 1-2 sprays per nostril twice per day at 137 µg/spray. Azelastine (brand names Astepro, 01.% or 0.15%) is usually used 1-2 sprays per nostril twice per day. Olopatadine (brand names Patanase) is usually used 2 sprays per nostril twice per day at 665 µg/spray. Loratadine (Claritin) is given orally as one 10 mg tablet or reditab, or 2 teaspoonfuls (10 mg) of syrup once daily.

For anticholinergics, ipratropium bromide is used to treat the symptom of rhinorrhea (runny nose) that is associated with seasonal allergic and non-allergic or vasomotor rhinitis. Ipratropium bromide, brand names Atrovent Nasal Spray 0.03% and Ipratropium Nasal Spray 0.06%, is usually used 2 sprays per nostril 2 to 3 times per day. Ipratropium (Atrovent nasal) Nasal Spray 0.06% is a metered-dose, manual pump spray unit which delivers 42 µg ipratropium bromide (on an anhydrous basis) per spray (70 µL) in an isotonic, aqueous solution with pH-adjusted to 4.7. The recommended dose of ATROVENT® (ipratropium bromide) Nasal Spray 0.06% is two sprays (84 µg) per nostril three or four times daily (total dose 504 to 672 µg/day) in adults and children age 12 years and older. Optimum dosage varies with response of the individual patient. The recommended dose of ATROVENT® Nasal Spray 0.06% for children age 5-11 years is two sprays (84 µg) per nostril three times daily (total dose of 504 µg/day).

For decongestants, oxymetazoline is used to reduce nasal swelling. Oxymetazoline, 0.025% and 0.05% solution, are usually used 2-6 drops per nostril twice per day For cromolyn, it may take 1 to 4 weeks to become fully effective. Because of this, cromolyn sodium is considered more useful in preventing allergy symptoms and is not viewed to be as effective as other medicines at treating rhinitis symptoms after they have already started. Furthermore, cromolyn sodium must be taken up to 4 times each day for it to work well, which makes compliance difficult. 40 mg/ml cromolyn, in 13 or 26 ml metered spray containers. Each metered actuation delivers 5.2 mg cromolyn sodium.

For leukotriene antagonist such as montelukast, the standard dose for 15 years and older is one 10-mg tablet; for 6 to 14 years is one 5-mg chewable tablet; for 2 to 5 years is one 4-mg chewable tablet or 4-mg oral granules; for 6 to 23 months is one packet of 4-mg oral granules.

For antibiotics such as penicillin, the standard dose for adult is 500 mg 4 times a day. For augmentin, the standard dose for adult is 500 mg 3-4 times a day. For a cephalosporin such as cephalexin, the standard dose for adult is 500 mg 4 times a day. For erythromycin, the standard adult dose is 500 mg 2-4 times a day.

The following examples further illustrate the present invention. These examples are intended merely to be illustrative of the present invention and are not to be construed as being limiting.

EXAMPLES

Example 1

A deionized water solution of rhamnolipids (JBR 515, a mixture of R1 and R2) at 15% concentration was obtained from Jeneil Biosurfactant Co., LLC (Saukville, Wis.). The rhamnolipid solution was diluted in water to 0.5% (w/w) and applied to a subject that suffered from perennial rhinitis. The same 0.5% (w/w) rhamnolipid formulation was also used in Examples 3-8.

The 0.5% rhamnolipid formulation was applied to the subject. A standard Q-Tip was dipped into the 0.5% rhamnolipid formulation and then the Q-Tip was applied gently onto the intranasal areas of the subject; the subject's intranasal area had eschars due to excessive mechanical rubbing of the assessable intranasal areas with paper handkerchiefs for excessive itching and nasal discharge associated with his perennial rhinitis.

The symptoms of his allergic rhinitis (nasal congestion, nasal hypersecretion, and sneezing) disappeared almost immediately for approximately 4 hours.

After 4 hours on the day of the first administration, the subject re-administered the same amount of rhamnolipid solution into both nostrils at approximately 2200 h, but as far into the intranasal space as was comfortable and swiped the intranasal surfaces that could be comfortably assessed. The subject repeated this on the opposite side, again using a standard Q-tip soaked with the 0.5% rhamnolipid formulation. The subject then went to bed a short time later and noticed that, in contrast to his normal state, his nose was not congested and nasal passages were completely clear. The subject could breathe easily and was told that he did not snore, which was highly unusual for the subject.

The subject continued treatment with this same formulation twice daily for more than 14 days. Shortly prior to administration of a new dose of the above-mentioned formulation, the subject's symptoms of allergic rhinitis (especially nasal congestion, nasal hypersecretion, and sneezing) reappeared and then, subsequent to renewed administration of the formulation, the symptoms rapidly disappeared. His snoring has virtually ceased and he feels much more vigilant throughout the day while receiving rhamnolipid formulation as described above.

Example 2

Objective

The objective of this study was to evaluate the efficacy of rhamnolipid in treating rhinitis in an animal model.
Material
Animal:
Female BALB-c mice each weighing 20-30 grams were used in this study.
Sensitization:
The followings were used to sensitize the mice:
1. 0.5 ml saline (0.9% sodium chloride), containing 25 μg of OVA (grade V, Sigma Chemical Co., St. Louis, Mo., USA) and 2 mg of aluminum hydroxide (alum) (pH 5.5, 308 mOsmol $L^{-1}$) were used as intraperitoneal injection;
2. 5 μl of 5% ovalbumin solution in saline was instilled in each nostril. Isoflurane (an anesthetic agent) was given prior to the intranasal administrations.
Rhamnolipids:
5 μl of 0.5% rhamnolipids (ABI-100, a mixture of rhamnolipid 1 and rhamnolipid 2) in saline was administered for each nostril.
Method
Mice were sensitized by 5 weekly intraperitoneal injection of ovalbumin (at Day 1, 8, 15, 22, and 29). After the 5 weekly intraperitoneal injections, from Day 32-50, mice were given 19 once-daily intranasal doses of ovalbumin (5 μl of 5% ovalbumin solution in saline instilled in each nostril). The mice were anesthetized using isoflurane prior to the intranasal instillation of ovalbumin.

On Day 49, 20 mice were assigned to a treatment group and a placebo group. The mice in the treatment group received 5 μl of a 0.5% rhamnolipid mixture in saline per nostril. This intranasal dose was administered twice, with the doses administered 1 hour apart. Mice were observed for signs of nasal irritation for a 15 minute continuous evaluation period, on the day of treatment (Day 49), and the day following treatment (Day 50). Half of the mice were also evaluated two days after treatment (Day 51). The investigators were blinded to the identity of the agent, i.e., which mice had received saline and which mice had received active treatment.

The number of sneezes and nose rubbings were counted. Nose rubbings were only counted if both paws were employed, and multiple rubbings in one quick succession were counted as one nose-rubbing event. The total (symptom) score was defined as the total number of sneezes and nose rubbings.
Results The means, standard deviations (SD), and standard errors (SE) of total (symptom) score in the placebo and treatment groups are recorded in Table 1.

TABLE 1

| | Ovalbumin-sensitized animals treated with Saline (Placebo Group) | | | | Ovalbumin-sensitized animals treated with Rhamnolipid (Treatment Group) | | | |
|---|---|---|---|---|---|---|---|---|
| | No. of Mice | Total Score Mean | SD | SE | No. of Mice | Total Score Mean | SD | SE |
| Day 1 after Treatment | 10 | 13.9 | 5.6 | 1.8 | 10 | 8.9 | 3.4 | 1.1 |

Day 1 After Treatment

One hour after renewed intranasal instillation of the OVA allergen on the first day after rhamnolipid application (Day 50), the average total symptom score in the treatment group was 8.9, compared to 13.9 in the control group. The difference in the total scores between the placebo and treatment groups was statistically significant (P=0.0269).
Conclusions:

This study shows rhamnolipids were effective in treating allergic rhinitis in a mouse model. Rhamnolipids resulted in a statistically significant reduction of total rhinitis symptom score in the treatment group when compared with the control group one day post-treatment.

Example 3

The 0.5% (w/w) rhamnolipid formulation (same as that described in Example 1) was applied to a healthy male, 66 years old, who had a history of mild nasal congestion. The rhamnolipid formulation was applied to the subject as 2 intranasal administrations, separated by 5 minutes, using Q-Tips soaked in the rhamnolipid formulation (a new Q-tip for every application). Each Q-Tip was dipped into the 0.5% rhamnolipid formulation and then applied by the subject gently onto the intranasal surfaces of the subject. The subject reported within minutes of dosing that his nasal passages were clearer, and this feeling lasted for 4 hours.

Example 4

The 0.5% (w/w) rhamnolipid formulation was applied to a healthy male (48 years of age), who had no history of allergic rhinitis, and had a history of mild nasal congestion prior to application. The 0.5% rhamnolipid formulation was applied to the subject as 2 intranasal administrations, separated by 5 minutes, using Q-Tips soaked in the rhamnolipid formulation (a new Q-tip for every application). Each Q-Tip was dipped into the 0.5% rhamnolipid formulation and then applied by the subject gently onto the intranasal surfaces of the subject.

Upon application, the subject reported a slight tingling (more noticeable after administration), 'medicinal' smell, 'moistening' sensation; all those symptoms subsided within 1-2 minutes. He noted that subsequently both nasal passages were more open than usual. One hour post-dose he noticed remarkably open nasal passages ('the clearest they've ever been'), and this sensation lasted until 18 hours post-dose.

Example 5

A healthy 61 year old male, with no pertinent medical history, specifically no allergic rhinitis, noted that beginning symptoms of a 'head-cold' might have started. The subject noticed a scratchy throat but nothing else, specifically: no rhinorrhea, no nasal congestion, itching or sneezing. The 0.5% rhamnolipid formulation was applied to the subject as 2 intranasal administrations, separated by 5 minutes, using Q-Tips soaked in the rhamnolipid formulation (a new Q-tip for every application). Each Q-Tip was dipped into the 0.5% rhamnolipid formulation and then applied by the subject gently onto the intranasal surfaces of the subject.

Subsequent to self-application of the rhamnolipid solution, the subject described a 'soothing and mentholated' sensation. The subject did not notice any tingling, any form of local irritation, rhinorrhea, nasal congestion, itching or sneezing. One hour after dosing, the subject noted that his nasal passages were more open than usual and this feeling lasted for 17 hours post-dosing and he experienced no rhinorrhea, no nasal congestion, itching or sneezing. The symptom of head-cold was still confined to throat: no 'scratchiness', but productive cough.

Example 6

A 49 year old female with recurrent sinusitis (three events that required treatment within the 2 months preceding rhamnolipid application) self-applied rhamnolipid topically. She complained of moderate rhinorrhea and severe nasal congestion. The 0.5% rhamnolipid formulation (same as that described in Example 1) was applied to the subject as 2 intranasal administrations, separated by 5 minutes, using Q-Tips soaked in the rhamnolipid formulation (a new Q-tip for every application). Each Q-Tip was dipped into the 0.5% rhamnolipid formulation and then applied by the subject gently onto the intranasal surfaces of the subject. This was repeated twice daily for ten days.

By the second day of rhamnolipid application, the subject reported a significant improvement of her symptoms. By day 3, the subject reported virtually complete alleviation of symptoms of sinusitis that lasted during the entire course of rhamnolipid application and even 3 days beyond the date at which rhamnolipid application was stopped.

Example 7

A 54 year old female with mild rhinorrhea and moderate nasal congestion (suspected non-allergic rhinitis) was described as a moderate snorer by her spouse. She self-applied a 0.5% rhamnolipid formulation as 2 intranasal administrations, separated by 5 minutes, using Q-Tips soaked in the rhamnolipid formulation (a new Q-tip for every application). Each Q-Tip was dipped into the 0.5% rhamnolipid formulation and then applied by the subject gently onto the intranasal surfaces of the subject. This was repeated twice daily for 14 days.

By the evening of the second day of application, the symptoms of rhinorrhea and nasal congestion were completely alleviated in the subject. Further, according to her spouse, the subject virtually stopped snoring. The subject noted that she awakened much more refreshed than usual from a night's sleep. Although the subject had symptoms of a common cold on day 7, she did not experience any nasal congestion as she usually would have, and her general symptoms of the common cold subsided after 2 days. After completion of the 14 days of rhamnolipid application, the alleviation of signs of mild rhinorrhea, moderate nasal congestion, and snoring continued for 3 days.

Example 8

A 24 year old male with a long history of allergic rhinitis with severe congestion and mild rhinorrhea self-applied a 0.5% rhamnolipid formulation as 2 intranasal administrations, separated by 5 minutes, using Q-Tips soaked in the rhamnolipid formulation (a new Q-tip for every application). Each Q-Tip was dipped into the 0.5% rhamnolipid formulation and then applied by the subject gently onto the intranasal surfaces of the subject. This was a single dose application. Symptoms of congestion were almost totally alleviated within 4 hours, with a concomitant transient increase in rhinorrhea. In the evening of the day of application, the subject complained of somewhat greater than normal congestion that improved during the night. Beginning the next day, his nose was totally free for the first time in months and this lasted for approximately 36 hours.

Example 9

Objective

The objective of this study is to compare the treatment effect of the invention in a cohort of 5-20 volunteers with a history of allergic rhinitis to their standard treatment.
Subjects Subjects are 18-70 years of age with a history of allergic rhinitis (acute or perennial allergic rhinitis which are taking intra-nasally applied antihistamines or corticosteroids.
Test Protocols Volunteers first have their TNSS (a standard rhinitis symptom score) established prior to their use of their standard medication and then again after approximately four hours.

The TNSS is the sum of four nasal symptom scores (runny nose, nasal congestion, itchy nose, and sneezing), each evaluated by the subject on a 0-3 scale. The TNSS can range from 0 to 12 total points.

Changes in TNSS before and after standard treatment and the difference in TNSS score before and after rhamnolipid is compared.

Whenever the volunteers subsequently require their standard treatment after their initial dose of the usual intranasal treatment, the same volunteers receive a single dose of rhamnolipid formulation at a concentration of 0.25, 0.5, or 1%. Each dose administration is delivered as 1-2 swipes of the formulation applied either as drops or via a Q-Tip to all assessable intranasal surfaces.
Evaluation Criteria TNSS scores prior to and at 4 hours after the administration of the standard treatment and then prior to and 4 hours after administration of rhamnolipid administration are assessed.

After each dose administration, a questionnaire is completed for each subject documenting their symptom score prior to administration and then after 4 hours and any discomfort or undue sensations they may have observed that are different between the two administrations.

The results are summarized in tabular form.

Example 10

Objective

The objective of this study is to compare the treatment effect of the invention in a cohort of 5-20 volunteers with a history of allergic rhinitis to their standard treatment.

Subjects

Subjects are 18-70 years of age with a history of allergic rhinitis (acute or perennial allergic rhinitis which are taking intra-nasally applied antihistamines or corticosteroids.

Test Protocols

Volunteers first have their TNSS (a standard rhinitis symptom score) established prior to their use of their standard medication and then again after approximately four hours.

The TNSS is the sum of four nasal symptom scores (runny nose, nasal congestion, itchy nose, and sneezing), each evaluated by the subject on a 0-3 scale. The TNSS can range from 0 to 12 total points.

Changes in TNSS before and after standard treatment and the difference in TNSS score before and after rhamnolipid is compared.

Whenever the volunteers subsequently require their standard treatment after their initial dose of the usual intranasal treatment, the same volunteers receive a single dose or multiple doses of rhamnolipid formulation at a concentration of 0.125, 0.25, 0.5, or 1% in combination with a corticosteroid, an antihistamine, an anticholinergic agent, a leukotriene antagonist, cromolyn, or a decongestant of 10-100% of the recommended dose of the individual marketed compound. Each dose of the rhamnolipid formulation and the formulation containing antihistamine, an anticholinergic agent, a leukotriene antagonist, cromolyn, or a decongestant is delivered intranasally, either in the form of micropipette application of a solution, drops, a gel, aerosol, emulsion, or other suitable to assessable intranasal surfaces.

Evaluation Criteria

TNSS scores prior to and at 4 hours after the administration of the standard treatment and then prior to and 4 hours after administration of rhamnolipid administration are assessed. After each dose administration, a questionnaire is completed for each subject documenting their symptom score prior to administration and then after 4 hours and any discomfort or undue sensations they may have observed that are different between the two administrations. The results are summarized in tabular form.

Example 11

Objective

The objective is to assess repeated doses of rhamnolipid on efficacy and morphological effects on mucosa of chronic administration of rhamnolipid formulation in a rodent model of allergic rhinitis.

An animal model involves a 7-14-day, randomized, double-blind comparison of repeated doses (1-5 doses per day, as guided by the response of the individual animals) of a dose of rhamnolipid nasal spray (0.25, 0.5% or 1.0% w/w) or placebo in rodents. Each group has 5-15 animals. The following or similar established model is used: Six- to 8-week-old BALB/c mice is sensitized by means of intranasal (local) application of ovalbumin (OVA) or systemic intraperitoneal injection. The animals are then challenged with intranasal OVA, and allergic response is assessed.

Efficacy of Treatment

The primary endpoints of the trial are histological and immunological changes in nasal mucosa samples. Histology of the upper and lower airways assess degree of cellular infiltration into mucous and tissue.

Results of the trial are assessed using standard statistical methods to depict trends and analyze responses to determine any statistical differences between placebo and rhamnolipid group's outcomes. Significance of any improvement is analyzed ($p<0.05$) of the rhamnolipid dose groups compared to placebo.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A method for treating a rhinitis or a sinusitis in a subject, comprising the steps of:
   identifying a subject suffering from the rhinitis or the sinusitis; administering intranasally to the subject a formulation comprising a pharmaceutically acceptable carrier and a rhamnolipid as the only active ingredient in an effective amount, whereby the symptoms of rhinitis or sinusitis in the subject are reduced.

2. The method according to claim 1, wherein said rhamnolipid is selected from the group consisting of: rhamnolipid 1, rhamnolipid 2, and the combination thereof.

3. The method according to claim 1, wherein said effective amount is 0.005-10% (w/w).

4. The method according to claim 1, wherein said effective amount is 0.02-5% (w/w).

5. The method according to claim 1, wherein the rhinitis is allergic rhinitis, infectious rhinitis, non-allergic rhinitis, or mixed allergic and non-allergic rhinitis.

6. The method according to claim 5, wherein the allergic rhinitis is perennial allergic rhinitis or seasonal allergic rhinitis.

7. The method according to claim 1, wherein the method is for treating rhinitis.

8. The method according to claim 1, wherein the method is for treating sinusitis.

9. The method according to claim 7, wherein the method reduces one or more symptoms selected from the group consisting of nasal congestion, nasal discharge, sneezing, and itching of the nose and throat in the subject.

10. The method according to claim 8, wherein the method reduces one or more symptoms selected from the group consisting of nasal congestion, rhinorrhea, sneezing, and nasal itching in the subject.

* * * * *